DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED FEBRUARY 2, 1971

883 O.G. 10

T883,008

NOVEL COMPOSITION OF MATTER 1,2,4-TRIS (PHENOXY) BENZENE

Gether Irick, Jr., Lloyd P. Foster, Jr., and Robert W. Kennedy, all of P.O. Box 511, Kingsport, Tenn. 37662

Continuation of application Ser. No. 701,565, Jan. 30, 1968. This application Mar. 19, 1970, Ser. No. 19,536

Int. Cl. C07c *43/22*

U.S. Cl. 260—613

No Drawing. 9 Pages Specification

A new polyphenyl ether, 1,2,4-tris(phenoxy)benzene is disclosed which possesses definite advantages such as oxidative stability and low melting point, making it an excellent high temperature heat transfer agent, lubricant, hydraulic fluid, diffusion pump oil and specialty processing fluid. The ratio of cross section of a molecule of 1,2,4-tris(phenoxy)benzene to length is relatively low, resulting in a good viscosity-temperature relationship. A good viscosity-temperature relationship is needed to provide as constant a viscosity as possible over a wide temperature range, thereby facilitating easy equipment design in regard to flow, lubricity, etc. The compound may also be blended with linear polyphenyl ethers to improve the properties thereof.